(12) United States Patent
Johannison

(10) Patent No.: US 9,844,614 B2
(45) Date of Patent: Dec. 19, 2017

(54) WOUND THERAPY DEVICE

(71) Applicant: Mölnlycke Health Care AB, Göteborg (SE)

(72) Inventor: Ulf Johannison, Landvetter (SE)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 346 days.

(21) Appl. No.: 14/431,785

(22) PCT Filed: Oct. 1, 2013

(86) PCT No.: PCT/EP2013/002938
§ 371 (c)(1),
(2) Date: Mar. 27, 2015

(87) PCT Pub. No.: WO2014/053232
PCT Pub. Date: Apr. 10, 2014

(65) Prior Publication Data
US 2015/0258259 A1    Sep. 17, 2015

Related U.S. Application Data

(60) Provisional application No. 61/708,081, filed on Oct. 1, 2012.

(30) Foreign Application Priority Data

Oct. 1, 2012 (EP) ..................... 12186750

(51) Int. Cl.
*A61M 1/00* (2006.01)
*A61F 13/00* (2006.01)

(52) U.S. Cl.
CPC ..... *A61M 1/0086* (2014.02); *A61F 13/00068* (2013.01); *A61M 1/0088* (2013.01); *A61F 2013/00357* (2013.01)

(58) Field of Classification Search
CPC .............. A61M 1/0086; A61M 1/0088; A61M 2039/1016; A61M 2025/0006;
(Continued)

(56) References Cited

U.S. PATENT DOCUMENTS 8,545,467 B2    10/2013    Larsson
2003/0097091 A1*    5/2003    Hobbs ................. A61M 1/3653
604/43
(Continued)

FOREIGN PATENT DOCUMENTS

DE    10 2011 055782 A1    5/2013
WO    WO-1999/013793 A1    3/1999
(Continued)

OTHER PUBLICATIONS

Oxford Dictionary definition of "sharp", https://en.oxforddictionaries.com/definition/us/sharp.*
(Continued)

*Primary Examiner* — Tatyana Zalukaeva
*Assistant Examiner* — Jessica Arble
(74) *Attorney, Agent, or Firm* — Ballard Spahr LLP

(57) ABSTRACT

This relates to a wound therapy device, including an outer part and an inner part facing surface provided with an inner part facing opening, and a first connection channel to establish fluid communication between the inner part facing opening and a connector opening adapted to be connected to an external device. The wound therapy device can also be a part of a wound therapy arrangement, which can further include, a wound filler, an external device, a wound cover film, and tubing connections. Methods of using the wound therapy arrangement are also disclosed.

17 Claims, 6 Drawing Sheets

(58) Field of Classification Search
CPC ..... A61F 13/00068; A61F 2013/00357; B65D 5/746–5/749
See application file for complete search history.

(56) References Cited

U.S. PATENT DOCUMENTS

| | | | |
|---|---|---|---|
| 2003/0970910 | 5/2003 | h | |
| 2007/0219500 A1* | 9/2007 | Wright | A61M 25/02 604/174 |
| 2014/0107577 A1* | 4/2014 | Boyd | A61M 5/3213 604/111 |

FOREIGN PATENT DOCUMENTS

| | | | | |
|---|---|---|---|---|
| WO | WO-2008/002773 A2 | 1/2008 | | |
| WO | WO 2008002773 A2 * | 1/2008 | .......... | A61M 1/0088 |
| WO | WO-2008/027449 A2 | 3/2008 | | |
| WO | WO-2009/002260 A1 | 12/2008 | | |
| WO | WO-2010/085270 A1 | 7/2010 | | |
| WO | WO-2010/094957 A1 | 8/2010 | | |
| WO | WO-2011/087871 A2 | 7/2011 | | |
| WO | WO 2011087871 A2 * | 7/2011 | ............. | A61F 13/02 |
| WO | WO-2013/010907 A1 | 1/2013 | | |
| WO | WO-2013/043972 A1 | 3/2013 | | |
| WO | WO-2013/093380 A1 | 6/2013 | | |

OTHER PUBLICATIONS

Oxford Dictionary definition of "pierce", https://en.oxforddictionaries.com/definition/us/pierce.*
International Search Report and Written Opinion dated Jan. 30, 2014 for International Patent Application No. PCT/EP2013/002938, which was filed Oct. 1, 2013 and published as WO 2014/053232 on Apr. 10, 2014 (Inventor—Johannison // Applicant—Molnlycke Health Care AB) (16 pages).
International Preliminary Report on Patentability dated Apr. 7, 2015 by the International Searching Authority for International Patent Application No. PCT/EP2013/002938, which was filed on Oct. 1, 2013 and published as WO/2014/053232 (Inventor—Ulf Johannison; Applicant—Mölnlycke HealthCare AB) (10 pages).

* cited by examiner

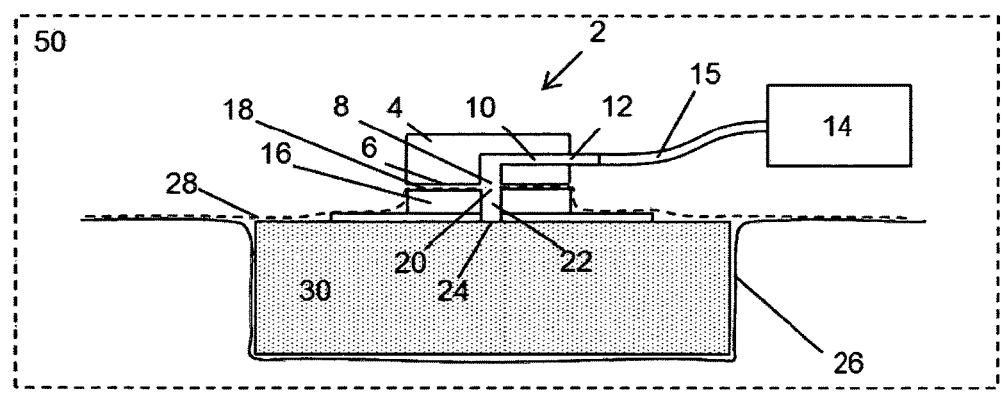
FIG. 1
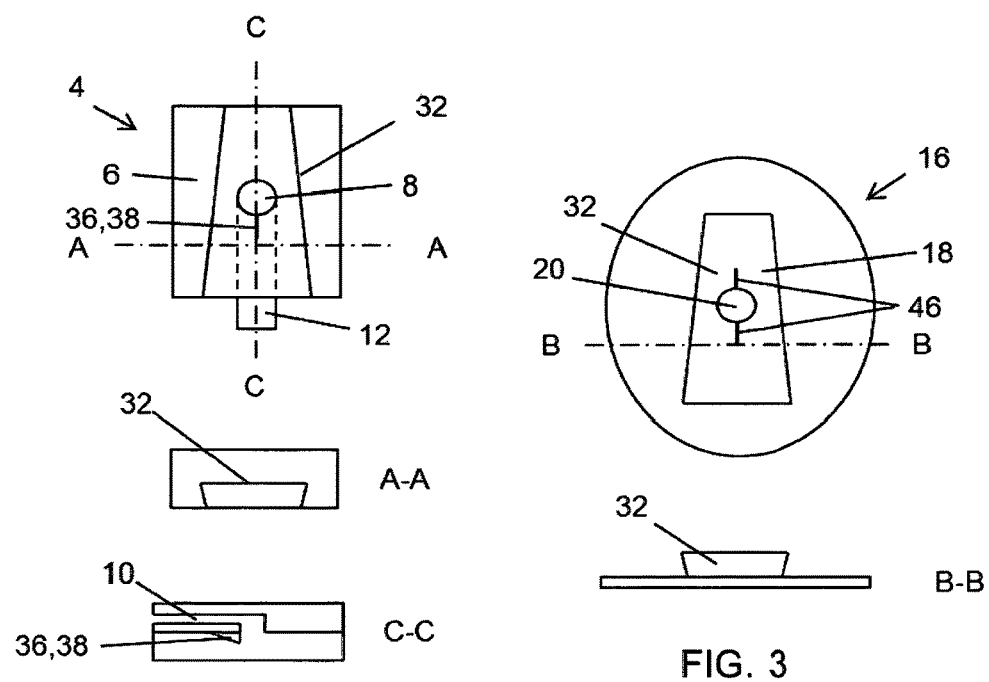
FIG. 2
FIG. 3

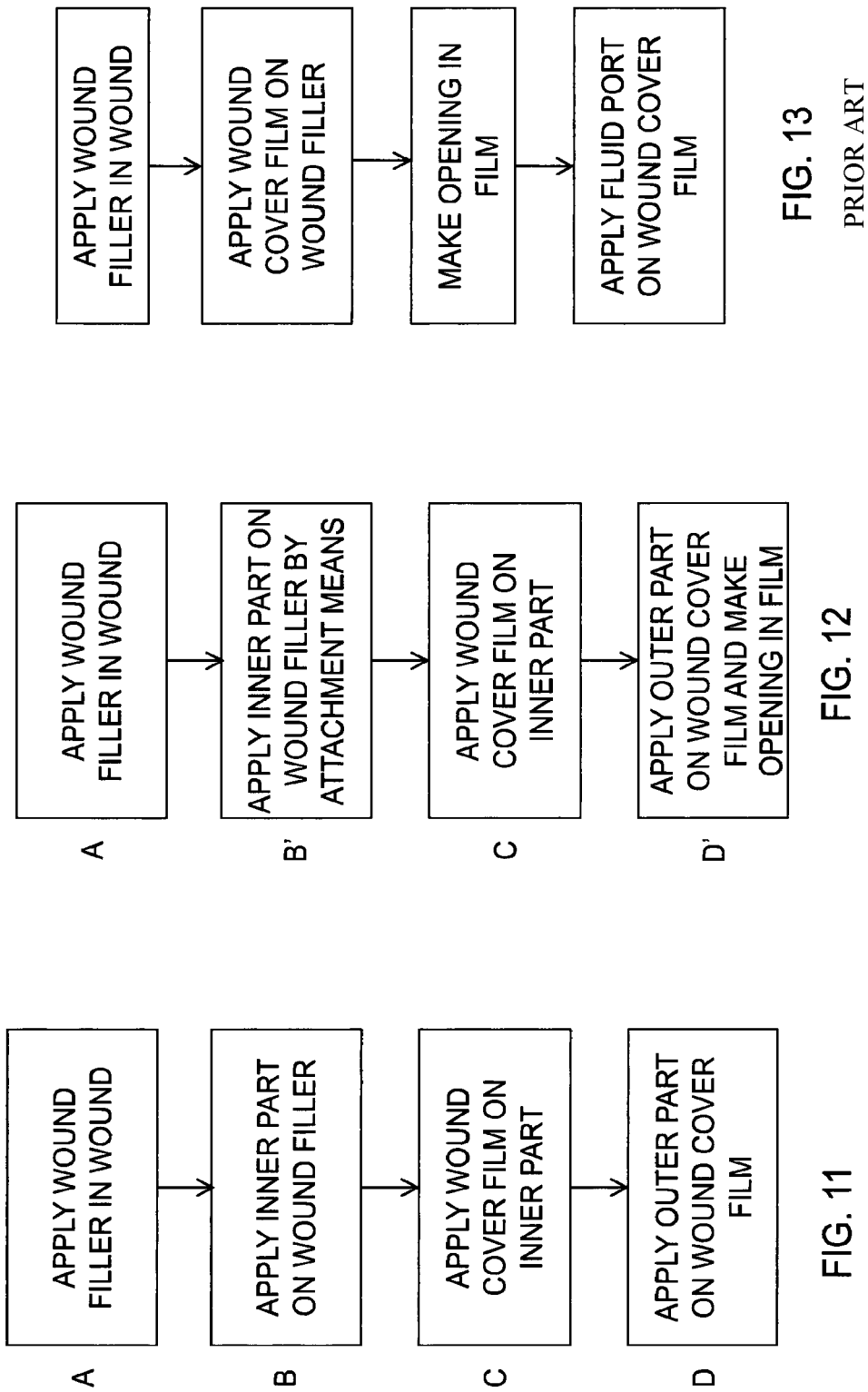

WOUND THERAPY DEVICE

CROSS-REFERENCE TO RELATED APPLICATIONS

This application is a U.S. National Phase Application of International Application No. PCT/EP2013/002938, filed on Oct. 1, 2013, which claims priority to European Patent Application No. 12186750.1, filed Oct. 1, 2012, and U.S. Provisional Application No. 61/708,081, filed Oct. 1, 2012, each of which are hereby incorporated by reference in their entirety.

TECHNICAL FIELD

The present disclosure relates to a wound therapy device, and a wound therapy arrangement, according to the preambles of the independent claims. The disclosure also relates to a method of using the wound therapy arrangement.

BACKGROUND

In the medical field there are many types of wounds that require treatment. In some instances they are post-operative wounds, but in other instances they can be open wounds that cannot yet be closed, as where infection sites exist, where open wounds require periodic application of medicine, or where the wounds are chronic non-healing pressure ulcers, venous ulcers, diabetic ulcers or where the wounds are too large to close surgically and must be allowed to heal on their own. In such cases, it is known that it can be desirable from the point of wound treatment, to apply a negative pressure or suction to the wound to remove fluids and exudates from the wound.

Various techniques to promote healing of a wound involve providing suction to the wound. For example, a vacuum source may serve to carry wound exudates away from the wound, which may otherwise harbour bacteria that inhibit the body's natural healing process. One particular technique for promoting the body's natural healing process may be described as negative pressure wound therapy (NPWT). This technique involves the application of a reduced pressure, e.g. sub-atmospheric, to a localized reservoir over a wound. Sub-atmospheric pressure has been found to assist in closing the wound by promoting blood flow to the area, thereby stimulating the formation of granulation tissue and the migration of healthy tissue over the wound. This technique has proven effective for chronic or non-healing wounds, but has also been used for other purposes such as post-operative wound care.

The general NPWT procedure provides for covering the wound with a flexible cover layer or film, also denoted surgical draper, such as a polymeric film, for example, to establish a vacuum reservoir over the wound where a reduced pressure may be applied by individual or cyclic evacuation procedures. To allow the reduced pressure to be maintained over time, the cover layer may include an adhesive periphery that forms a substantially fluid tight seal with the healthy skin surrounding the wound.

Although some procedures may employ a micro-pump contained within the vacuum reservoir, most NPWT treatments apply a reduced pressure using an external vacuum source. Fluid communication must therefore be established between the reservoir and the vacuum source. To this end, a fluid port is often coupled to the cover layer to provide an interface for a fluid conduit extending from the external vacuum source. The fluid port typically exhibits a degree of rigidity, which provides for a convenient reception of the fluid conduit. WO-1999/013793 and WO-2009/002260 disclose typical examples of NPWT treatment devices. In WO-1999/013793 is disclosed a surgical drape and suction head for wound treatment. The surgical drape and the suction head combination is used for attaching the suction head to the wound area. And, in WO-2009/002260 is described a device for treatment of wounds with reduced pressure that comprises a sealing film, which is placed sealingly around the wound to cover the wound, an under-pressure source, as well as a tube, which connects a space over the wound and beneath the sealing film to the under-pressure source.

In some prior art arrangements, which some have been described above, the fluid port may project somewhat from the surrounding skin, and may thus tend to cause discomfort for patients as the fluid port is inadvertently pressed into the wound. This tendency is particularly evident when a fluid port is used on wounds on a patient's back, heel or other locations where pressure points develop as the patient reclines or sits. Accordingly, in some occasions, it may be advantageous to position the fluid port at a location remote from the wound, and to draw fluid from the wound to the remotely positioned fluid port. Such a technique is often referred to as a bridging arrangement; see e.g. WO-2010/085270 which in particular relates to a method and apparatus for bridging from a dressing in negative pressure wound therapy.

In WO-2010/085270 is also disclosed a wound dressing provided with a contact layer positioned in direct contact with a bed of a wound. A wound filler is positioned in the wound over the contact layer and is intended to allow the wound dressing to absorb, capture and/or wick wound exudates. The wound dressing also includes a cover layer to be positioned over the wound to form a substantially fluid-tight seal with the surrounding skin. The cover layer includes an aperture through which wound fluids and atmospheric gases may be removed from the dressing under the influence of a reduced pressure. A fluid port having a flange is arranged to facilitate connection of the wound dressing to a fluid conduit. The fluid port is affixed to the dressing e.g. by means of an adhesive on the underside of the flange.

Thus, a wound filler, having a three-dimensional shape is adapted to the shape of the wound and placed in the wound. Thereafter an airtight wound cover film, provided with a suitable adhesive on the surface adapted to face the skin, is arranged to hold the wound filler in the required position by attaching the wound cover film to the healthy skin around the wound to keep wound filler in position. If a negative pressure wound therapy is to be used an aperture must be made in the wound cover film in order to apply the negative pressure. The aperture, or opening, is made e.g. by a pair of scissors to manually make a hole in the film to gain connection to covered wound filler. Then a fluid port is attached to the film such that an air-tight fluid connection is established between the wound and an external device, e.g. a negative pressure wound therapy device.

This known procedure is schematically illustrated by the flow diagram in FIG. 13. The last step in addition includes peeling away a protective film on the adhesive, aiming and then pressing the fluid port such that the opening in the fluid port corresponds to the aperture made in the film.

The present inventor has identified that some improvements may be preferred for the presently used device. One is related to that it is sometimes difficult to assure that the openings in the fluid port and the wound cover film correspond, which may be beneficial in order to achieve an air tight connection.

In addition, the adhesive used at the surface of the fluid port in order to attach it to the wound cover film may, in some occasions, result in leakage problems in the interface between the edge of the fluid port and the cover film.

Thus, one object of the present disclosure is to provide for an airtight connection between a fluid port and an opening in the wound cover film.

A further object is to achieve a way of attaching a fluid port to a wound cover film without using an adhesive.

Another object of the present disclosure is to overcome or ameliorate at least one of the disadvantages of the prior art, or to provide a useful alternative.

SUMMARY

At least one of the above-mentioned objects is achieved by the present disclosure according to the independent claims.

As such, the present disclosure relates to a wound therapy device, comprising
- an outer part comprising a connector opening adapted to be connected to an external device, the outer part being adapted to be at least partially located on a first side of a wound cover film,
- an inner part adapted to be at least partially located on a second side, opposite of the first side, of the wound cover film,
- the wound therapy device being such that the outer part and the inner part are adapted to be attached to one another, by means of a locking means of the wound therapy device, with the wound cover film arranged therebetween and such that the connector opening is in fluid communication with a wound therapy volume that is at least partially delimited by the second side of the wound cover film.

Optionally, the locking means comprises a snap-on connection, at least a portion of the snap-on connection being adapted to be located on the first side of the wound cover film when the locking means attaches the outer part to the inner part.

By virtue of the fact that at least a portion of the snap-on connection is adapted to be located on the first side of the wound cover film when in a locking condition, an appropriate possibility to determine whether or not the snap-on connection is in a locking condition or not may be obtained. For instance, an operator, such as a clinician, may be able to determine, e.g. visually or haptically, whether or not the snap-on connection is in an engaged condition without necessarily needing access to the volume that is enclosed by the wound cover film.

As used herein, the expression "snap-on connection" refers to a connection between a plurality of connecting portions, wherein at least one of the portions is adapted to snap into position and fit to another portion. Generally, at least one of the portions is adapted to deform during a mounting procedure. When a desired relative position between a plurality of connecting portions is obtained, the deformable portion, at least partially, abandons its deformed state, resulting in that first abutment means, arranged in connection with the first portion, engages with abutment means on the other connecting portion. In a snap-on connection, either one of the plurality of connecting portions can be equipped with a portion adapted to deform during a mounting procedure. In reality, a snap-on connection can be provided in which several connecting portions each one of which having a portion adapted to be deformed during a mounting phase.

Optionally, the snap-on connection comprises an elastically deformable protrusion connected to the outer part. As used herein, the expression "elastically deformable protrusion" relates to a protrusion at least a portion of which is adapted to be displaced, without any part of the protrusion being subjected to permanent deformation, as the snap-on connection assumes its locking condition.

By virtue of the fact that the elastically deformable protrusion is connected to the outer part, it may be possible for a user to release the outer part from the inner part without necessarily having to break the wound cover film.

Optionally, the elastically deformable protrusion comprises an elastically deformable hook attached to the outer part, the hook comprising a proximal end adapted to undergo the elastic deformation and a distal end adapted to cooperate with an inner abutment surface connected to the inner part.

Optionally, the elastically deformable hook and the outer part form a unitary component.

Optionally, the elastically deformable protrusion comprises a plurality of the hooks.

Optionally, the wound therapy device comprises a conduit portion, the conduit portion comprising a first conduit portion and a second conduit portion wherein, when the outer part and the inner part are attached to one another with the wound cover film arranged therebetween, the first conduit portion is located on the first side of the wound cover film, the second conduit portion is located on the second side of the wound cover film and the conduit portion is in fluid communication with the connector opening.

Optionally, the conduit portion is attached to the outer part.

Optionally, the wound therapy device is adapted to be used for a wound area that has an extension in a wound extension plane, the locking means being such that the outer part is adapted to be attached to the inner part by displacing the outer part relative to the inner part in a direction that is substantially parallel to a direction in the wound extension plane.

Optionally, the device further comprises a hole making means arranged on the outer part and/or inner part and being adapted to make an opening in the wound cover film arranged between the outer part and inner part before or as the outer part and inner part are attached to one another.

Optionally, the hole making means is an integrated part of the outer part.

Optionally, the hole making means comprises at least one cutting edge arranged on the outer part.

Optionally, the inner part is provided with fixating means, or a fixator, adapted to fixate the inner part in relation to the wound.

Optionally, the locking means is adapted to apply a force between the inner and outer parts to ensure an airtight sealing of the fluid communication.

Optionally, the inner part is adapted to be arranged at a wound filler.

Optionally, the locking means comprises a dovetail joint type.

Optionally, the locking means comprises magnetic material arranged at the outer part and the inner part.

Optionally, the external device is a negative pressure source device.

A second aspect of the present disclosure relates to a wound therapy kit comprising a wound cover film and the wound therapy device according to the first aspect of the present disclosure.

A third aspect of the present disclosure relates to a wound therapy arrangement comprising the wound therapy device according to the first aspect of the present disclosure, a wound filler, a wound cover film, an external device, preferably a negative pressure source device, and a connection arrangement for connecting the external device to the wound therapy device.

A fourth aspect of the present disclosure relates to a wound therapy device, comprising an outer part comprising an inner part facing surface provided with an inner part facing opening, and a first connection channel to establish fluid communication between said inner part facing opening and a connector opening adapted to be connected to an external device, e.g. a negative pressure wound therapy device. The device further comprises an inner part comprising an outer part facing surface provided with an outer part facing opening, and a second connection channel to establish fluid communication between said outer part facing opening and an opening adapted to be arranged in connection with a wound, wherein said inner part is adapted to be arranged under a wound cover film in relation to the wound. Furthermore a locking means is provided which is adapted to attach and lock said outer part to said inner part, having said wound cover film arranged between said parts, and such that said inner part facing opening and outer part facing opening are positioned to essentially correspond to each other.

Optionally, it is assured that the openings in the fluid port and the wound cover film corresponds, which is essential in order to achieve an air tight connection. In short, this is achieved by attaching and locking the outer part to the inner part using the locking means.

Optionally, the fluid port may be attached to a wound cover film without using an adhesive, which also is achieved by attaching and locking the outer part to the inner part using the locking means. In particular this is an improvement in relation to the known technique where the fluid port was attached to the wound cover film with an adhesive.

Thus, the sealing effect, referred to in the first aspect, is achieved by the irreversible lock and air tight fit between the inner and outer parts in combination with the sealing obtained by the wound cover film. In particular, as the wound cover film is provided with an adhesive at the surface facing the wound, and thus the inner part. Thereby, an even safer and more user friendly system is achieved.

SHORT DESCRIPTION OF THE APPENDED DRAWINGS

FIG. 1 is a cross-sectional view of the wound therapy device according to the present invention.

FIG. 2 illustrates different views of the outer part according to one embodiment of the present invention.

FIG. 3 illustrates different views of the inner part according to one embodiment of the present invention.

FIGS. 11 and 12 are flow diagrams illustrating methods according to present invention.

FIG. 13 is a flow diagram illustrating a known method.

DETAILED DESCRIPTION OF PREFERRED EMBODIMENTS OF THE INVENTION

Figure 4:
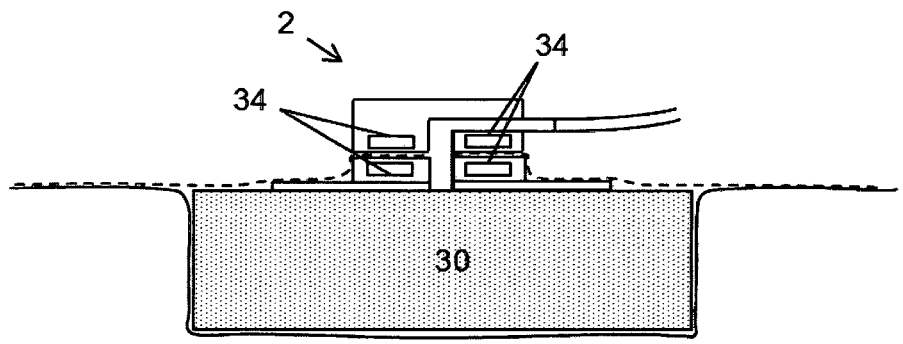
FIG. 4 is a cross-sectional view of a wound therapy device according to another embodiment of the present invention.

The present invention will now be described in detail with references to the appended drawings. Throughout the drawings, the same reference signs have been used to indicate the same or a similar feature.

Thus, FIG. 1 illustrates an embodiment of a wound therapy device 2 comprising an outer part 4 comprising an inner part facing surface 6 provided with an inner part facing opening 8, and a first connection channel 10 to establish fluid communication between the inner part facing opening 8 and a connector opening 12 adapted to be connected to an external device 14 using an appropriate tubing connection 15. Preferably, the external device 14 is a negative pressure source device, e.g. of the kind which has been described in the background section.

The FIG. 1 wound therapy device 2 further comprises an inner part 16 comprising an outer part facing surface 18 provided with an outer part facing opening 20, and a second connection channel 22 to establish fluid communication between the outer part facing opening 20 and an opening 24 adapted to be arranged in connection with a wound 26. The inner part 16 is adapted to be arranged under a wound cover film 28 in relation to the wound 26. Often a so-called wound filler 30 is used to fill up the wound. This has also been described in the background section.

In addition, the wound therapy device comprises a locking means 32 (see FIGS. 2 and 3) adapted to attach and lock the outer part 4 to the inner part 16, having the wound cover film 28 arranged between these parts, and such that the inner part facing opening 8 and the outer part facing opening 20 are positioned to essentially correspond to each other.

Any of a variety of wound covers compatible with negative pressure wound treatment systems can be used. Generally, the wound cover is adapted to be attached to the skin surrounding the wound, and, either alone or in combination with one or more other components of the negative pressure system, forms an airtight seal over the wound. Non-limiting examples of suitable wound covers include plastic films, e.g. polyurethane films. The wound cover can be attached to the skin surrounding the wound, for example, by means of an adhesive. Wound covers may comprise an adhesive, and/or by used with an adhesive that is applied just before use. Examples of adhesives that may be used include, but are not limited to, acrylic adhesives and/or silicone gel adhesives. In some embodiments, the adhesive or adhesives is/are already incorporated as part of the wound cover. In some embodiments, the adhesive or adhesives is/are applied to the wound cover member during use.

For example, a suitable wound cover is AVANCE™ Transparent Film sold by Mölnlycke Health Care AB, which is a polyurethane film with an acrylic adhesive. Also suitable for use in embodiments of the invention is AVANCE™ Film with SAFETAC™ technology (also sold by Mölnlycke Health Care AB), which comprises a layer of perforated polyurethane coated on one side with silicone gel. As a non-limiting example, the adhesive sold under the trademark MEPISEAL™ by Mölnlycke Healthcare AB may be used for attaching the wound cover member to the skin surrounding the wound.

As a non-limiting example, the wound cover film may be a transparent film which is a polyurethane (PU) ester film having a mat finish, with a thickness between approximately 22-30 μm and coated with a polyacrylate adhesive. Moreover, and again purely by way of example, the wound cover film may come with an applicator film made of transparent polyethylene (PE) with a thickness of approximately 45-55 μm. Purely by way of example, such a wound cover film could have a density of approximately 100 g/cm$^3$.

As another non-limiting example, the wound cover film could have a PU ether film instead of a PU ester film, and come with an applicator film based on a copolymer of PE and PP (polypropylene). Such a PU film could be, like for the above example, coated with a polyacrylate adhesive and have a mat finish. The PU film would have a thickness of approximately 26-30 μm. The applicator for the upgraded film would have an expected thickness of approximately 40 μm. Purely by way of example, such a wound cover film could have a density of approximately 80 g/cm$^3$.

FIGS. 2 and 3 illustrate different views of the outer part and inner part, respectively, according to one embodiment of the present invention.

At the top in FIG. 2 a view of the outer part 4 from below is shown, where the inner part facing surface 6, the inner part facing opening 8 and the connector opening 12 is indicated. Below is shown a cross-section along line A-A, and at the bottom is shown a cross-section along line C-C.

At the top in FIG. 3 a view of the inner part 16 from above is shown, where the outer part facing surface 18 provided with an outer part facing opening 20 is indicated.

At the bottom is shown a cross-section along line B-B.

In one embodiment the locking means 32 is of a dovetail joint type, which is illustrated in FIGS. 2 and 3. The outer part 4 is provided with an elongated indentation having walls that slightly incline outwards such that the indentation is slightly wider in a direction away from the inner part facing surface 6, see FIG. 2, middle drawing. In addition, the indentation has a wider end and a narrower end seen along C-C. Herein the wider end is at the same end as the connector opening 12, but the opposite is naturally also possible. The inner part 16 has a corresponding locking means 32 which is embodied as an elongated protrusion having a shape which mates with the indentation at the outer part.

The outer part 4 is adapted to be attached to the inner part 16 by the locking means 32 by applying a sliding movement of the outer part 4 in relation to the inner part 16, thereby essentially avoiding applying vertical forces, but also rotational and shear forces, to the wound. If the inner and outer parts are oriented as in FIGS. 2 and 3, the inner part is arranged in connection with the wound and the outer part is moved downwards in relation to the inner part in order to attach the parts to each other using the dovetail joint type connection.

As such, the dovetail joint illustrated in FIGS. 2 and 3 comprises contact surfaces of the outer part 4 and the inner part 16, wherein these contact surfaces are inclined in two directions, viz a first direction from the inner part facing surface 6 when the parts 4, 16 are attached to one another and a second direction that extends substantially in the plane of the inner part facing surface 6. The inclination in the first direction may imply an appropriate locking in a direction to or from the plane of the inner part facing surface 6. Moreover, the inclination in the second direction may for instance imply that the inner part facing opening 8 and the outer part facing opening 20 are aligned when the parts 4, 16 are attached to one another.

According to another embodiment the locking means 32 is embodied by magnetic material 34 arranged at the outer part and at the inner part, and that these parts are adapted to be attached to each other by magnetic forces. This embodiment is illustrated by FIG. 4. The magnetic material pieces are arranged such that the required position between the outer and inner parts is achieved. In FIG. 4 two pieces are arranged at each of the parts. It is naturally possible to have more or fewer magnetic pieces. By having more magnetic pieces an even higher precision in the positioning may be achieved.

A preferred aspect is that the locking means 32 provides for applying a force between the inner and outer parts to ensure an airtight sealing of the fluid communication. This may achieved by the dove tail joint embodiment by adapting the sizes and shapes of the protrusion and indentation to each other such that the required force between the inner and outer parts is obtained. For the magnetic embodiment discussed hereinabove, the airtight sealing may be achieved by selecting magnetic material(s) such that the appropriate magnetic forces are obtained which in turn may result in an airtight sealing of the fluid communication.

Figure 6:
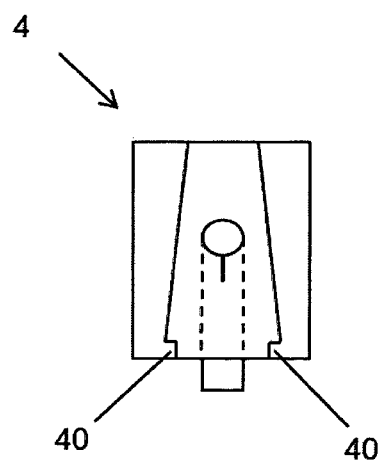
FIG. 6 illustrates the outer part according to still another embodiment of the present invention.

According to a further embodiment the locking means 32 is adapted to irrevocably lock the outer part to the inner part. This may e.g. be achieved by providing projections 40 (see FIG. 6) in relation to the indentation at the outer part 4 such that the protrusion of the outer part is locked when the widest part of the protrusion has passed by the projections. A presumption is that the outer part is made from a material having some flexibility allowing the projections to flex out allowing the protrusion to pass by.

Preferably the locking means is adapted to generate an acknowledgement receipt, e.g. a click sound, when the outer part is correctly attached to the inner part. This may be achieved according to the embodiment illustrated in FIG. 6 when the projections 40 flexes back when the protrusion is in place.

Figure 5:
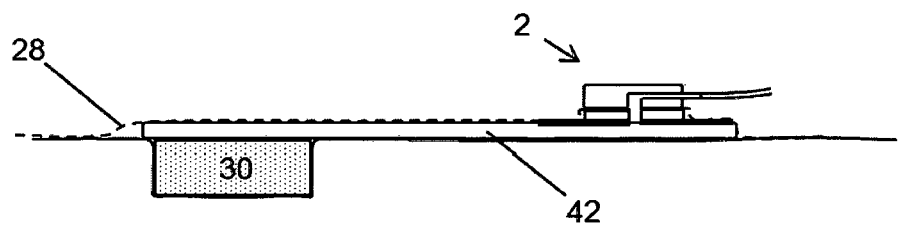
FIG. 5 illustrates the wound therapy device according to the present invention used in a bridging arrangement.

As illustrated in e.g. FIGS. 1 and 4 the inner part 16 is adapted to be arranged at a wound filler 30. Within the scope of the invention, as defined by the appended claims, it is also possible to arrange the wound therapy device at a distance from the wound by using a bridging arrangement. This may be applied for wounds at places where less space is available, e.g. at the back or at a heel. FIG. 5 schematically illustrates the use of the wound therapy device in relation to a bridging arrangement 42. The bridging arrangement 42, the wound filler 30 and the inner part of the wound therapy device 2 are held in place by a wound cover film 28 and the outer part is then attached to the inner part as described above.

A presumption to establish an airtight fluid communication between the first and second connection channels is that an opening is made in the wound cover film. It is naturally possible to manually make this opening, e.g. by use of a scalpel, a pair of scissors etc., when the wound cover film 28 is attached to the skin holding the inner part in place.

According to another embodiment the wound therapy device further comprises a hole making means 36 (see FIG. 2) arranged at the inner part 16 and/or at the outer part 4 and being adapted to make an opening in the wound cover film 28 arranged between the outer part and inner part, such that the opening is positioned to essentially correspond to the openings in said outer part and inner part to establish an airtight fluid communication between the connector opening 12 and the opening 24 facing the wound.

Preferably, the opening in the wound cover film 28 is made during the procedure of attaching the outer part 4 to the inner part 16.

The hole making means 36 is, according to one embodiment, an integrated part of the outer part 4 and comprises e.g. at least one cutting edge 38 (see FIG. 2) arranged at the outer part close to the inner part facing opening. A slit 46 (see FIG. 3) is provided in the inner part to receive the cutting edge 38.

Figure 7:
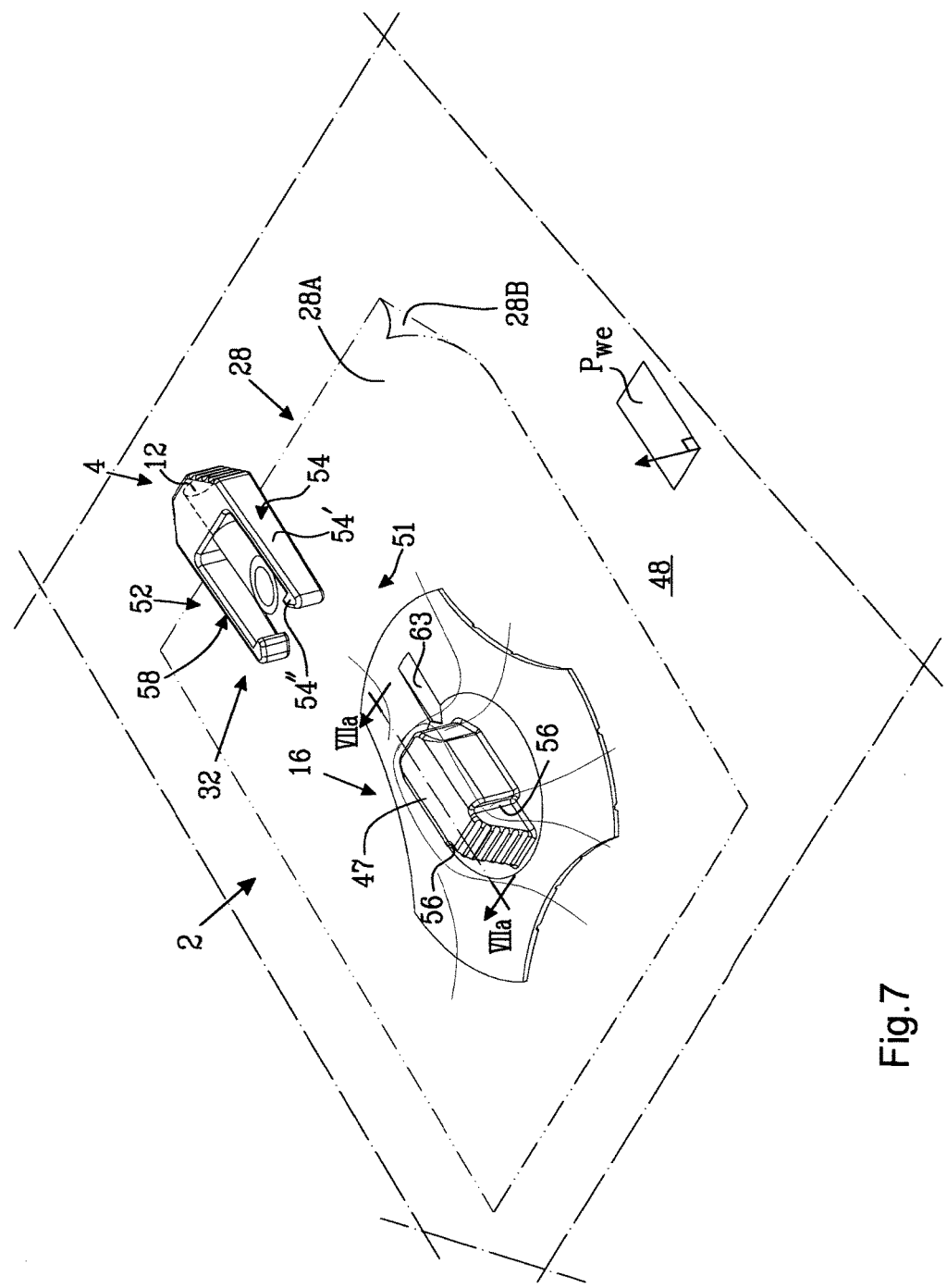
FIG. 7 is a perspective view of another embodiment of the wound therapy device.

FIG. 7 illustrates another embodiment of the wound therapy device 2. As may be gleaned from FIG. 7, the embodiment disclosed therein comprises an outer part 4 comprising a connector opening 12 adapted to be connected to an external device (not shown in FIG. 7). Purely by way of example, the external device may be a negative pressure source device as is indicated in FIG. 1 for instance.

The outer part 4 is adapted to be at least partially located on a first side 28A of a wound cover film 28. Moreover, the FIG. 7 wound therapy device 2 comprises an inner part 16 adapted to be at least partially located on a second side 28B, opposite of the first side 28A, of the wound cover film 28. Generally, the second side 28B of the wound cover film 28 is adapted to face the wound (not shown in FIG. 7) when in use.

As for the other embodiments of the wound therapy device 2 presented hereinabove, the inner part 16 of the FIG. 7 embodiment is adapted to be arranged at a wound filler (not shown in FIG. 7).

The wound therapy device 2 illustrated in FIG. 7 is such that the outer part 4 and the inner part 16 are adapted to be attached to one another, by means of a locking means 32 of the wound therapy device 2, with the wound cover film 28 arranged therebetween and such that the connector 12 opening is in fluid communication with a wound therapy volume 48 that is at least partially delimited by the second side 28B of the wound cover film 28.

In the embodiment illustrated in FIG. 7, the locking means 32 comprises a snap-on connection 51. At least a portion of the snap-on connection is adapted to be located on the first side 28A of the wound cover film 28 when the locking means 32 attaches the outer part 4 to the inner part 16.

In the embodiment of the wound therapy device 2 illustrated in FIG. 7, the snap-on connection 51 comprises an elastically deformable protrusion 52 connected to the outer part 4. In the implementation of the protrusion illustrated in FIG. 7, the elastically deformable protrusion 52 comprises an elastically deformable hook 54 attached to the outer part 4. The hook 54 comprises a proximal end 54' adapted to undergo the elastic deformation and a distal end 54" adapted to cooperate with an inner abutment surface 56 connected to the inner part 16.

Figure 7A:
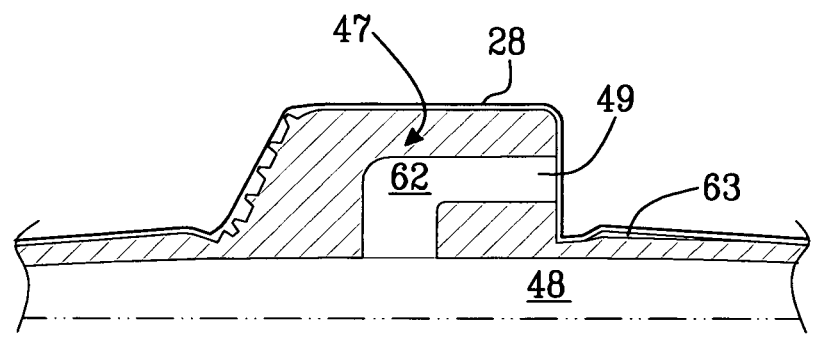
FIG. 7a is a cross-sectional view of the inner part of the FIG. 7 embodiment.

Purely by way of example, and as is illustrated in the FIG. 7 embodiment, in particular in FIG. 7a, the inner part 16 may comprise an inner protrusion 47 that protrudes in a direction from the wound when in use. The FIG. 7 inner protrusion 47 may comprise the inner abutment surface 56 that has been discussed hereinabove. Furthermore, the inner protrusion 47 may comprise an inner opening 49 adapted to receive a portion of the outer part 4. Moreover, the inner protrusion 47 is preferably adapted to provide a fluid communication between the inner opening 49 and the wound therapy volume 48. To this end, the inner protrusion 47 may comprise a cavity 62 that is in fluid communication with the inner opening 49 and which is adapted to be in fluid communication with the wound therapy volume 48.

In the implementation of the outer part 4 illustrated in FIG. 7, the elastically deformable hook 54 and the outer part 4 form a unitary component. However, it is also envisaged that in other implementations of the outer part 4, the hook 54 and the remaining portion of the outer part 4 may be separate components, and e.g. be of different materials, that are attached to one another in order to form the outer part 4.

It is further envisaged that implementations of the outer part 4 may comprise an elastically deformable protrusion that in turn comprises a plurality of elastically deformable hooks. To this end, reference is made to FIG. 7 which illustrates an embodiment of an elastically deformable protrusion 52 which comprises two elastically deformable hooks 54, 58.

The FIG. 7 embodiment of the wound therapy device 2 is adapted to be used for a wound area that has an extension in a wound extension plane $P_{we}$. Moreover, in the FIG. 7 embodiment, the locking means 32 is such that the outer part 4 is adapted to be attached to the inner part 16 by displacing the outer part 4 relative to the inner part 16 in a direction that is substantially parallel to a direction in the wound extension plane $P_{we}$.

In the FIG. 7 embodiment, the locking means 32 is such that the outer part 4 is adapted to be attached to the inner part 16 by displacing the outer part 4 relative to the inner part 16 in a rectilinear direction that is substantially parallel to a direction in the wound extension plane $P_{we}$.

Embodiments of the wound therapy device may comprise a conduit portion. To this end, reference is made to FIG. 8 which illustrates a bottom view of the FIG. 7 implementation of the outer part 4. As may be gleaned from FIG. 8, the conduit portion 60 may be connected to, or even form part of, the outer part 4. Moreover, and as is intimated in FIG. 8, the conduit portion 60 may comprise a first conduit portion 60' and a second conduit portion 60" wherein, when the outer part 4 and the inner part (not shown in FIG. 8) are attached to one another with the wound cover film arranged therebetween, the first conduit portion 60' is located on the first side of the wound cover film, the second conduit portion 60" is located on the second side of the wound cover film and the conduit portion is in fluid communication with the connector opening 12.

As such, when the outer part 4 and the inner part are attached to one another with the wound cover film arranged therebetween, the conduit portion 60 will extend through the wound cover film.

Embodiments of the wound therapy device 2 may comprise a hole making means arranged on the outer part 4 and/or the inner part 16 and being adapted to make an opening in the wound cover film arranged between the outer part and inner part before or as the outer part and inner part are attached to one another. For instance, the implementation of the outer part 4 illustrated in FIG. 8 comprises a cutting edge 38. In fact, in the FIG. 8 implementation of the outer part 4, the cutting edge 38 is obtained by virtue of the fact that the conduit portion 60 has an end surface 61 that is oblique with respect to the extension direction $ED_{cp}$ of the conduit portion. Purely by way of example, a normal to the end surface 61 of the conduit portion 60 may form an angle with the extension direction $ED_{cp}$ of the conduit portion which angle is at least 45°, alternatively at least 60°.

The fact that the end surface 61 is oblique with respect to the extension direction $ED_{cp}$ implies that only small portion of the conduit portion 60 will firstly pierce through the wound cover film and that the cross-sectional area of the conduit portion 60 that passes the wound cover film will gradually increase as it is moved through the film.

In order to further facilitate the piercing of the wound cover film, the cutting edge 38, i.e. the apex of the conduit portion 60, may be sharp. Purely by way of example, if the outer part 4 is manufactured by moulding, such as injection moulding wherein a curable material is injected into a mould, the mould (not shown) may have a shape that results in a sharp apex of the conduit portion 60. As another non-limiting example, instead of, or in addition to, the above discussed shape of the mould, the sharpness of at least the apex of the conduit portion 60 may be obtained by means of post-treatment of the conduit portion 60. As a non-limiting example, at least the apex of the conduit portion 60 may be grinded after the moulding procedure such that an appropriately sharp cutting edge 38 is obtained.

As a non-limiting example, the end surface 61 of the conduit portion 60 may be substantially perpendicular to the wound extension plane $P_{we}$. As such, a normal to the end surface 61 may extend in a plane that is parallel to the wound extension plane $P_{we}$. Such an extension of the end surface 61 of the conduit portion 60 may imply that the outer part 4 may be inserted into an inner part in two orientations, i.e. an orientation such as the one illustrated in FIG. 8 or upside down, but the conduit portion 60 may nevertheless be able to make an opening in the wound cover film and may also be able to provide a fluid communication between the connector opening 12 and the wound therapy volume 48 when the outer part 4 and the inner part 16 are connected to one another.

Figure 8:
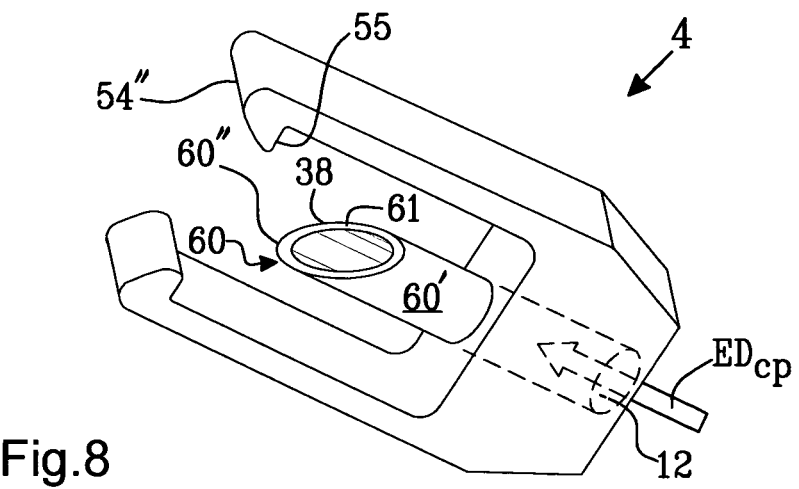
FIG. 8 is a perspective view of the outer part of the FIG. 7 embodiment.

The implementation of the outer part 4 illustrated in FIG. 8 may be adapted to be used in a wound therapy device 2 in which the outer part 4 is adapted to be connected to an inner part (not shown in FIG. 8) by a rectilinear displacement of the outer part 4 relative to the inner part 16 in a direction that is substantially parallel to the extension direction $ED_{cp}$ of the conduit portion. To this end, the distal end 54" of the elastically deformable hook 54 may comprise an outer abutment surface 55, adapted to cooperate with an inner abutment surface of the inner part, which outer abutment surface 55 extends in a plane that is substantially perpendicular to the extension direction $ED_{cp}$ of the conduit portion.

In order to facilitate the insertion of the conduit portion 60 into the inner opening 49, the inner part 16 may comprise a guide, such as the guide groove 63 illustrated in FIG. 7, which is adapted to guide the conduit portion 60 to the inner opening 49 during a connection procedure.

Figure 9:
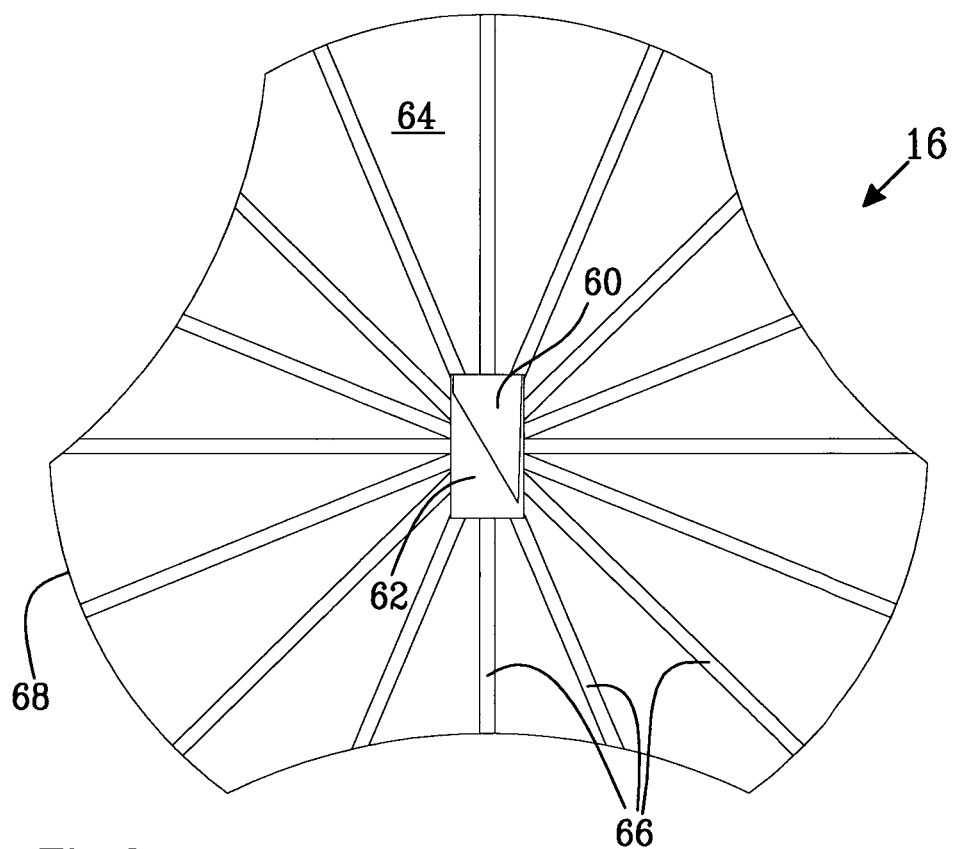
FIG. 9 is a bottom view of the FIG. 7 embodiment.

FIG. 9 illustrates a bottom view of FIG. 7 wound therapy device 2 when the outer part 4 and the inner part 16 are locked to one another. FIG. 9 illustrates the previously discussed cavity 62 into which a portion of the conduit portion 60 may extend when the inner part 16 and the outer part 4 are connected to one another. Purely by way of example, the protrusion 47 of the inner part 16 that has been discussed hereinabove with reference to FIG. 7 may accommodate the cavity 62. As such, as compared to the embodiments of the wound therapy device 2 that have been discussed hereinabove with reference to FIGS. 2 to 5, the embodiment that is illustrated in FIGS. 7 to 9 may provide a fluid communication between an external device and the wound therapy volume without the need for aligning an opening of the outer part 4 with an opening of the inner part 16.

Furthermore, FIG. 9 illustrates an implementation of the inner part 16 which comprises a panel 64 and a plurality of reinforcing ribs 66 each one of which extending over a portion of the panel 64. In the FIG. 9 implementation of the inner part 16, each one of the ribs 66 extends from the cavity 62 towards the periphery 68 of the panel 64. Purely by way of example, each one of the ribs 66 may have a uniform thickness, i.e. an extension in a direction normal to the plane in which the panel 64 extends, from the cavity 62 towards the periphery 68. In another non-limiting example, the thickness of each one of the ribs 66 may decrease towards the periphery 68.

It is envisaged that embodiments of the wound therapy device 2 may comprise a locking means 32 that instead of, or in addition to, the snap-on connection 51 discussed hereinabove with reference to FIGS. 7 to 9, may comprise at least one of the following locking means implementations: the dovetail joint type that has been discussed hereinabove with reference to FIGS. 1 to 3 and the magnetic joint type that has been discussed hereinabove in relation to FIG. 4.

It is also envisaged that embodiments of the wound therapy device 2, such as the wound therapy device 2 illustrated in FIGS. 7 to 9, comprises neither a dovetail joint type nor a magnetic joint type.

Additionally, it is envisaged that embodiments of the of the wound therapy device 2 does not have the following features: an outer part comprising an inner part facing surface provided with an inner part facing opening, an inner part comprising an outer part facing surface provided with an outer part facing opening, and a locking means adapted to attach and lock the outer part to the inner part, having the wound cover film arranged between the parts, and such that the inner part facing opening and outer part facing opening are positioned to essentially correspond to each other.

Moreover, it is envisaged that embodiments of the of the wound therapy device 2, such as the embodiment of the wound therapy device 2 discussed hereinabove with reference to FIGS. 7 to 9, does not have all the features of appended claim 21. As such, although purely by way of example, it is possible to envisage a scope of protection of the wound therapy device 2 from which the scope of appended claim 21 is disclaimed.

Irrespective of the embodiment of the wound therapy device 2, the inner part 16 may be provided with a fixating means 44, or a fixator 44, adapted to fixate the inner part 16 in relation to the wound. Purely by way of example, the fixating means 44 may be fixedly attached to the inner part, for instance by means of an adhesive, a weld joint or similar.

Figure 10:
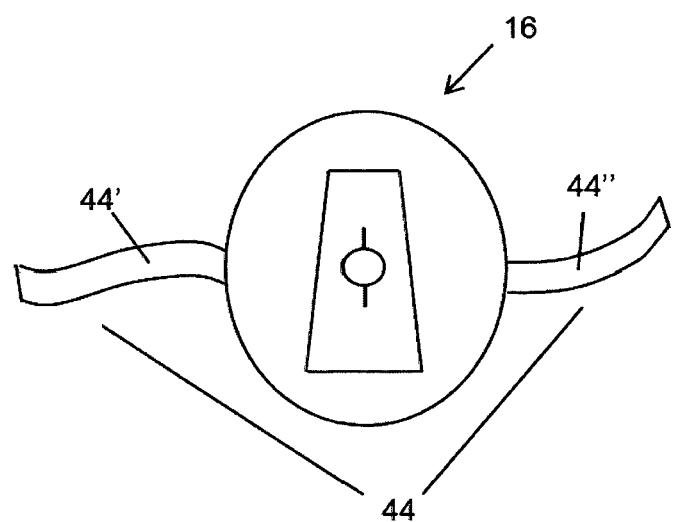
FIG. 10 is a top view of another implementation of an inner part.

An implementation of such a fixator is illustrated in FIG. 10. The FIG. 10 fixator is illustrated with an implementation of the inner part 16 that could form part of the FIG. 2 embodiment of the wound therapy device 2. However, and as has been indicated hereinabove, the fixator could be used for any implementation of the inner part 16. As is indicated in FIG. 10, the fixating means 44 comprised two elongate bands 44', 44" each one of which is adapted to extend from the inner part 16.

The fixating means 44, which may also be referred to as an attachment means 44, may comprise of one or many straps provided with e.g. Velcro or any other type of hook and loop attachment arrangement. As an alternative, the wound facing surface of the inner part may be provided with an adhesive.

As has been intimated hereinabove, the fixating means 44 may be adapted to fixate the inner part 16 in relation to the wound. For instance, the fixating means 44 could be adapted to fixate the inner part in relation to the wound filler (not shown in FIG. 9). However, implementations of the fixating means 44 may also be adapted to extend outside of the wound filler such that the fixating means may fixate the inner part 16 to the wound filler as well as fixating the wound filler to the wound (not shown in FIG. 9). To this end, though purely by way of example, the fixating means 44 may have a length of at least 5 cm, alternatively a length of at least 10 cm.

The inner and outer parts are preferably made of a suitable plastic material which may be heat sterilized. It may be preferred that the inner part is made of a softer material than the outer part. The inner part would then have a hardness in the range of 50-100 Shore, alternatively 65-95 Shore and preferably 65-85 Shore (according to the ASTM D2240 type A scale). This would be advantageous in that the inner part then better would conform to the surface of the skin or wound which reduces the impact on the wound, and reduces the discomfort for the patient. Another advantage is that it is then easier to attach the inner part in that the attachment means more securely may provide attachment of the inner part.

As a non-limiting example, the outer part could comprise or be constituted by at least one of the following materials: ABS (acrylonitrile butadiene styrene) or PP (polypropylene). The inner part may for instance comprise or be constituted by a thermo plastic elastomer such as PU (polyurethane) or PVC (polyvinyl chloride).

Moreover, although purely by way of example, each one of the outer part and the inner part may be manufactured by means of moulding, such as injection moulding.

The illustrated embodiments of the outer part have an essentially rectangular cross-sectional shape in a plane parallel to the inner part facing surface and have a thickness of less than 15 mm. Other shapes and sizes are naturally possible within the scope of the invention as defined by the claims.

The inner part preferably comprises a flat lower part having a first extension in a plane parallel to the patient's skin, and an upper part having a second extension in a plane parallel to the patient's skin, whereas the first extension is larger than the second extension in order to spread the bearing pressure.

To ensure the sealing function the contacting surfaces of the inner and outer parts may be provided with an embossed frame and a corresponding suppression adapted to receive the frame.

The present invention also relates to a wound therapy arrangement 50 (see FIG. 1) comprising the wound therapy device 2 provided with features described above, a wound filler 30, a wound cover film 28, an external device 14, preferably a negative pressure source device, and a tubing connection 15 for connecting the external device to said wound therapy device.

In addition the invention relates to a method of using said wound therapy arrangement. The method is schematically illustrated in the flow diagrams in FIGS. 11 and 12.

Thus, with reference to FIG. 8, the method is adapted for use in connection with a wound therapy arrangement that comprises the wound therapy device which has been described above, a wound filler, a wound cover film, an external device, preferably a negative pressure source device, and a tubing connection for connecting the external device to said wound therapy device. The method comprises the steps of:
  A—applying said wound filler in a wound;
  B—applying an inner part of said wound therapy device in connection to said wound filler;
  C—applying said wound cover film on said inner part, and
  D—applying an outer part of said wound therapy device on said film such that openings in said inner part and outer part essentially correspond.

If the external device is to be connected to the wound therapy device in order to apply a negative pressure to the wound an opening has to be made in the wound cover film between steps C and D. This is preformed either as a separate manual step or "automatically", when the outer part is attached to the inner part.

In a further refinement, which is illustrated in FIG. 12, step D in the method further comprises making an opening in said wound cover film, such that said opening is positioned to essentially correspond to the openings in said outer part and inner part. This refined step D is denoted D' in FIG. 9.

According to still a further refinement of the method, step B further comprises attaching said inner part by an attachment means. This refined step B is denoted B' in FIG. 12.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A wound therapy device, comprising
  an outer part comprising a connector opening adapted to be connected to an external device, said outer part being adapted to be at least partially located on a first side of a wound cover film,
  an inner part adapted to be at least partially located on a second side of said wound cover film, wherein said second side is opposite of said first side of said wound cover film,
  said wound therapy device being such that said outer part and said inner part are adapted to be attached to one another, by means of a locking means of said wound therapy device, with said wound cover film arranged therebetween and such that said connector opening is in fluid communication with a wound therapy volume that is at least partially delimited by said second side of said wound cover film,
wherein said locking means comprises a snap-on connection comprising an elastically deformable protrusion connected to said outer part, at least a portion of said snap-on connection being adapted to be located on said first side of said wound cover film when said locking means attaches said outer part to said inner part,
wherein said wound therapy device is adapted to be used for a wound area that has an extension in a wound extension plane ($P_{we}$), said locking means being such that said outer part is adapted to be attached to said inner part by displacing the outer part relative to the inner part in a rectilinear direction that is substantially parallel to a direction in said wound extension plane ($P_{we}$).

2. The wound therapy device according to claim 1, wherein said elastically deformable protrusion comprises an elastically deformable hook attached to said outer part, said elastically deformable hook comprising a proximal end adapted to undergo an elastic deformation and a distal end adapted to cooperate with an inner abutment surface connected to said inner part.

3. The wound therapy device according to claim 2, wherein said elastically deformable hook and said outer part form a unitary component.

4. The wound therapy device according to claim 2, wherein said elastically deformable protrusion comprises a plurality of said hooks.

5. The wound therapy device according to claim 1, wherein said wound therapy device comprises a conduit portion, said conduit portion comprising a first conduit portion and a second conduit portion wherein, when said outer part and said inner part are attached to one another with said wound cover film arranged therebetween, said first conduit portion is located on said first side of said wound cover film, said second conduit portion is located on said second side of said wound cover film and said conduit portion is in fluid communication with said connector opening.

6. The wound therapy device according to claim 5, wherein said conduit portion is attached to said outer part.

7. The wound therapy device according to claim 1, wherein said device further comprises a hole making means arranged on said outer part and/or said inner part and being adapted to make an opening in said wound cover film arranged between said outer part and said inner part before or as said outer part and inner part are attached to one another.

8. The wound therapy device according to claim 7, wherein said hole making means is an integrated part of said outer part.

9. The wound therapy device according to claim 8, wherein said hole making means comprises at least one cutting edge arranged on said outer part.

10. The wound therapy device according to claim 1, wherein said inner part is provided with a fixating means adapted to fixate said inner part in relation to a wound.

11. The wound therapy device according to claim 1, wherein said locking means is adapted to apply a force between said inner and outer parts to ensure an airtight sealing of the fluid communication between said connector opening and said wound therapy volume.

12. The wound therapy device according to claim 1, wherein said inner part is adapted to be arranged at a wound filler.

13. The wound therapy device according to claim 1, wherein said locking means comprises a dovetail joint.

14. The wound therapy device according to claim 1, wherein said locking means comprises a magnetic material arranged at said outer part and said inner part.

15. The wound therapy device according to claim 1, wherein said external device is a negative pressure source device.

16. A wound therapy kit comprising the wound cover film and the wound therapy device according to claim 1.

17. A wound therapy arrangement comprising the wound therapy device according to claim 1, a wound filler, an external device, and a connection arrangement for connecting the external device to said wound therapy device.

* * * * *